United States Patent [19]

Hatch

[11] Patent Number: 4,594,392

[45] Date of Patent: Jun. 10, 1986

[54] SYNERGISTICALLY STABILIZED MIXED FORM HALOGENATED AND/OR INTERHALOGENATED RESINS FOR DISINFECTING WATER

[75] Inventor: Gary L. Hatch, Sheboygan, Wis.

[73] Assignee: Ametek, Inc. - Plymouth Products Division, Sheboygana, Wis.

[21] Appl. No.: 794,313

[22] Filed: Nov. 1, 1985

Related U.S. Application Data

[63] Continuation of Ser. No. 679,201, Dec. 6, 1984, abandoned, which is a continuation-in-part of Ser. No. 579,532, Feb. 13, 1984, abandoned.

[51] Int. Cl.$^4$ .............................................. C08F 8/22
[52] U.S. Cl. .................................. 525/327.1; 525/356
[58] Field of Search .............................. 525/327.1, 356

[56] References Cited

U.S. PATENT DOCUMENTS

| | | | |
|---|---|---|---|
| 2,580,809 | 1/1952 | Marks et al. | 210/23 |
| 2,706,701 | 4/1955 | Beller et al. | 167/70 |
| 2,739,948 | 3/1956 | D'Alelio | 260/2.1 |
| 2,754,245 | 7/1956 | Hosmer | 167/70 |
| 2,853,417 | 9/1958 | Holliswood et al. | 167/33 |
| 3,101,250 | 8/1963 | Schoenbeck | 23/87 |
| 3,136,716 | 6/1964 | Kitter | 210/62 |
| 3,161,588 | 12/1964 | Zsoldos, Jr. | 210/64 |
| 3,316,173 | 4/1967 | Mills et al. | 210/62 |
| 3,346,446 | 10/1967 | Zsoldos, Jr. | 167/17 |
| 3,425,790 | 2/1969 | Sloan | 21/2 |
| 3,436,345 | 4/1969 | Goodenough et al. | 210/62 |
| 3,437,647 | 4/1969 | Freifeld | 260/88.3 |
| 3,462,363 | 8/1969 | Mills | 210/37 |
| 3,565,872 | 2/1971 | Katchalski et al. | 260/80.72 |
| 3,817,860 | 6/1974 | Lambert et al. | 210/29 |
| 3,923,665 | 12/1975 | Lambert et al. | 210/501 |
| 3,948,853 | 4/1976 | Horning | 210/62 |
| 4,187,183 | 2/1980 | Hatch | 210/501 |
| 4,190,529 | 2/1980 | Hatch | 210/24 |
| 4,223,110 | 9/1980 | Phillips et al. | 525/327.1 |
| 4,287,319 | 9/1981 | Phillips | 525/336 |
| 4,298,475 | 11/1981 | Gartner | 210/266 |
| 4,420,590 | 12/1983 | Gartner | 525/357 |

OTHER PUBLICATIONS

Article entitled, "Iodine for the Disinfection of Water", by Black et al, appearing in the Journal American Water Works Association, vol. 60, No. 1, Jan., 1968, Paper No. R6802, pp. 69–83.
Article entitled, "The Use of Active Iodine as a Water Disinfectant", by Shih L. Chang, appearing in the Journal of the American Pharmaceutical Association, Scientific Edition, Jun., 1958, pp. 417–423.
Article entitled, "The Germicidal Action of Iodine", by Wyss and Strandskov, appearing in vol. 6, Arch. Biochem., pp. 261–268 (1945).
Article entitled, "Modern Concept of Disinfection", by Shih L. Chang, appearing in the Journal of the Sanitary Engineering Division, ASCE, vol. 97, No. SA5, Proceeding Paper 8441, Oct., 19721, pp. 687–707.
Abstract entitled, "The Relative Bacteriocidal Activity of Hypoiodous Acid and Diatomic Iodine," appearing in the 1955 edition of Bactiological Proceedings, and designated A 15 at p. 23 thereof.
Chemical Abstract No. 67887z, entitled "Complexes of Halogen Molecules with Polymers and Copolymers", appearing in Chemical Abstracts, vol. 72, 1970, at p. 54.

*Primary Examiner*—Joseph L. Schofer
*Assistant Examiner*—Bernard Lipman
*Attorney, Agent, or Firm*—Andrus, Sceales, Starke & Sawall

[57] ABSTRACT

Synergically stabilized mixed form halogenated and/or interhalogenated forms of the freebase polyvinyl-pyridine resin for disinfecting water. The resins may be employed in a single pass column or bed system to provide instantaneous disinfection of bacterially contaminated water.

6 Claims, No Drawings

SYNERGISTICALLY STABILIZED MIXED FORM HALOGENATED AND/OR INTERHALOGENATED RESINS FOR DISINFECTING WATER

CROSS REFERENCE TO RELATED APPLICATION

This application is a continuation of application Ser. No. 679,201, filed Dec. 6, 1984, now abandoned, which is a continuation-in-part of application Ser. No. 579,532 filed Feb. 13, 1984 abandoned.

BACKGROUND AND SUMMARY OF THE INVENTION

The present invention relates to the on-contact, instantaneous disinfection of water, and more particularly to the use of synergically stabilized, mixed form halogenated and/or interhalogenated vinylpyridine resins for disinfecting water.

Several techniques employing resins are known for killing bacteria in water. The usual method involves treating the water with resins that provide halogen residuals such as $I_2$, $Br_2$, and $Cl_2$ for disinfection. Several methods involve the use of polyhalide anion exchange resins. Still another water disinfecting technique involves the use of an anion exchange resin loaded with insoluble triiodide ions ($I_3^-$). The following patents show examples of these techniques: U.S. Pat. Nos. 3,316,173; 3,425,790; 3,436,345; 3,462,363; 3,565,872; 3,817,860; 3,923,665; 4,187,183; 4,190,529; and 4,420,590.

Resins in accordance with the techniques noted above have the potential for releasing halide and polyhalide ions and do not produce an optimum halogenhypohalous acid mixture, and, as such, diminish their bactericidal efficiency. The resins of U.S. Pat. No. 3,565,872, though not made from anion exchange resins, also have these disadvantages, as well as the disadvantage for the potential for promoting resin decomposition in aqueous media, such as with the $Cl_2$—, $Br_2$—, and the BrCl—forms. Further, none of the above anion exchange resins generate hypohalous acid when treating water high in total dissolved salts with the exception of U.S. Pat. No. 4,187,183 which releases only very low levels of hypoiodous acid (less than 0.22 ppm HOI) under such circumstances. Hypoiodous acid is desirable since it is more bactericidal and more virucidal than iodine ($I_2$). Heretofore, significant levels of hypoiodous acid have had to be generated by either an iodinated anion exchange resin in combination with a scavenger system as in U.S. Pat. No. 4,187,183 or by adding an extraneous oxidant such as a chloramine as in U.S. Pat. No. 3,163,716 and U.S. Pat. No. 3,161,588. The interhalogenated resins in U.S. Pat. No. 3,565,872 produce hypohalous acids but not in an optimum disinfecting mixture with a corresponding halogen, e.g., $I_2$—HOI, $Br_2$—HOI, or $Br_2$—HOBr.

Therefore, a resin which provides for single pass, on-contact instantaneous disinfection, releases an optimum mixture of disinfecting levels of halogen and hypohalous acid without halide and polyhalide release, and which provides for long term resin stability in aqueous medium would be a significant improvement in water treatment technology.

Accordingly, it is an object of the present invention to provide synergistically stabilized, mixed form halogenated and/or interhalogenated polymeric, vinyl pyridine resins for single pass, on-contact instantaneous disinfection of water. It is another object to provide such resins as disinfectants capable of producing optimum disinfecting mixtures of halogen and hypohalous acid (e.g., HOBr or HOI through hydrolysis of the interhalogen, or through reaction of one halogen or interhalogen with another halogen) for universal disinfection against bacteria, viruses, and amoebic cysts. Still another object of the invention is to provide such resins for producing halide- and polyhalide-free effluents when treating water relatively high in salt content. Yet another object of the invention is to provide such resins that possess long term stability in an aqueous medium.

In accordance with these objects, granular or bead form, polymeric vinylpyridine resins which have been cross-linked with divinylbenzene, divinylpyridine, or other conventional crosslinking agent and which contain the pyridyl functional group covalently bonded to the vinyl polymeric backbone by the pyridyl No. 2 or No. 4 carbon are treated with a mixture of halogens and/or interhalogens to provide a media for disinfection of bacterially contaminated water. With the present invention, depending on the degree of loading of halogens and/or interhalogens on the vinylpyridine resin, instantaneous, single-pass flow-through disinfection can be achieved and a residual halogen and hypohalous acid (HOBr or HOI) is produced. If the residual halogen and hypohalous acid are to be reduced or removed, a simple follow-up scavenger column or bed of activated carbon can be employed.

The combined features of non-ionic complexation of the mixture of halogens and/or interhalogens with the pyridyl functional group and the hydrolysis of the interhalogens and/or reaction of one halogen or interhalogen with another halogen within the resin matrix precludes the ion exchange of halide ions ($I^-$ and $Br^-$) and polyhalide ions ($I_3^-$, $Br_3^-$, $I_2Cl^-$, etc.) which can occur in the previous state of the art disinfecting resins when they are challenged with water containing a high level of total dissolved salts. Minimizing the halide and polyhalide content of the effluent water provides for more potent disinfecting action and for a more physiologically acceptable potable water as pointing out in U.S. Pat. No. 4,420,590. The problem of excess halide (greater than 5–10 ppm) and polyhalide exchange from resins when treating water high in total dissolved salts can occur with resins prepared in accordance with the previous state of the art such as those resins in U.S. Pat. Nos. 3,565,872; 3,187,806; and 4,187,183. This problem is eliminated and does not occur with resins prepared in accordance with the present invention.

Because of the non-ionic complexation in the present invention, no iodide or bromide salt (e.g., KI or KBr) is needed in the preparation, thereby maximizing the disinfection efficiency of the total halogens and interhalogens. For example, in the $Br_3^-$, form of polyhalide resin such as in U.S. Pat. No. 3,462,363, one-third of the halogen is wasted just to provide for binding the negatively charged tribromide ion ($Br_3^-$), to the positively charged anion exchange resin.

Resins prepared in accordance with the present invention may be employed for swimming pool disinfection, emergency water disinfection kits, and small scale drinking water treatment systems with appropriate scavenging systems, as well as other applications where water disinfection is desired.

The unique features of this invention solve problems apparently not recognized in the prior art. These unique features are not characterized by the vinylpyridine-based polymers alone, but by their mixed form halogen and/or interhalogen molecular addition reaction products which, heretofore, have never been prepared and tested. Neither have the on-contact, bactericidal action and heretofore unknown synergistic stability of the mixed form resins been demonstrated; nor has their ability to produce effluents containing optimum mixtures of halogen and hypohalous acid been demonstrated. The synergistic stability of the mixed form resins, though not fully understood, is believed to be due to an inherent reduction-oxidation buffering phenomenon or "redox" equilibria occurring within the resin matrix and is believed to occur to some degree in all of the mixed form resins. Similar redox equilibria is defined by Light (T. S. Light, *Anal. Chem.*, 44, 1038 (1972)) and examples are given by Lambert et al. (*Anal. Chem.*, 47, 915 (1975)) and Black and Whittle (*J-AWWA*, 59, 607 (1967)).

The disclosures of the prior art, including U.S. Pat. No. 3,565,872, fail to provide any teachings of the present invention, and the advantages of the present invention as described above are, as a whole, believed to be unobvious and of a surprising and unexpected nature to one skilled in the art.

DESCRIPTION OF THE PREFERRED EMBODIMENT

In accordance with the present invention, a free base, vinyl polymeric resin (granular or bead-form) which has been crosslinked with divinylbenzene, divinylpyridine, or other conventional crosslinking agent and which contains the pyridyl functional group covalently bonded to the vinyl polymeric backbone by the pyridyl number 2 or number 4 carbon is reacted with a mixture of halogens and/or interhalogens to provide a media for on-contact, instantaneous single-pass disinfection of bacterially contaminated water. Instantaneous disinfection is accomplished within the resin bed because of the relatively high concentration of halogen and hypohalous acid (HOBr or HOI) at the surface of the granules or beads. If desired, the residual halogen and hypohalous acid can be reduced or removed by a simple follow-up scavenger column or bed of activated carbon.

The preparation of the free base, crosslinked virgin material (poly-2- and poly-4-vinylpyridine) is described in U.S. Pat. No. 2,739,948 and follows below:

Poly-2-vinylpyridine, Crosslinked

Crosslinked copolymers of 2-vinylpyridine are made in bead form by suspension polymerization in a pressure-tight autoclave by the following procedure. To the autoclave are added (parts are given in parts by weight):
0.18 part benzoyl peroxide-dissolved in vinylpyridine
0.05 part tert.-butyl perbensoate dissolved in vinylpyridine
90 parts 2-vinylpyridine
10 parts divinylbenzene (or 2,4-divinylpyridine, prepared as in U.S. Pat. No. 2,739,948)
200 parts distilled water
3 parts hydroxy apatite (sub-micronic particle size)
0.03 parts sodium oleate
The autoclave is then closed and agitated by a rocking mechanism while the autoclave is immersed in a controlled-temperature bath at 90° C. for about 7 hours and then at 113°–115° C. for about 3 hours. The resultant copolymer beads are washed with dilute hydrochloric acid to remove any suspension agent, then with dilute sodium hydroxide to remove adsorbed hydrochloric acid, then with water, and subsequently dried at 70° C. for about two hours.

Poly-4-vinylpyridine, Crosslinked

Follow the procedure above for poly-2-vinylpyridine but substitute an equimolar quantity of 4-vinylpyridine monomer for the 2-vinylpyridine monomer.

Also, poly-2- and poly-4-vinylpyridine (crosslinked) may be obtained from Reilly Tar & Chemical Corp., identified as LX-101 and R-8050, respectively.

The resin complexes of the present invention are comprised of the molecular addition reaction products formed from the reaction of the polymerized, free base pyridyl functional groups with a combination or mixture (two or more) of halogens ($I_2$ and $Br_2$) and/or interhalogens (ICl, IBr, and BrCl) such that all or a fraction of the pyridyl functional groups are complexed. The reaction or complexation of the polymerized free base pyridine resin (poly-4-vinylpyridine) and a mixture of a halogen ($I_2$) and interhalogen (ICl) may be illustrated by the following equation:

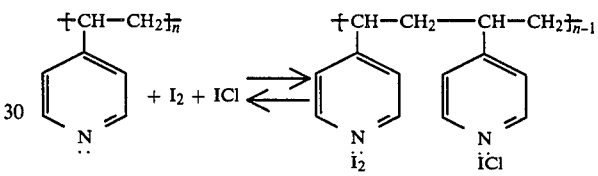

GENERAL PREPARATION PROCEDURE

The first step in preparing the complexed resin of the present invention is to calculate the equivalent weight of halogens and/or interhalogens needed to give the desired form and loading on the resin for a given weight of the dry virgin resin material. Then, add the appropriate mixture of halogens and/or interhalogens to a corrosion-proof vessel containing a compatible solvent such as methyl alcohol. When using bromine chloride (BrCl), a nonoxidizable solvent such as methylene chloride ($CH_2Cl_2$) or chloroform ($CHCl_3$) should be used. Allow for complete dissolution to occur, then add the dry resin directly to the alcohol solution. Continuous mixing of the resin slurry is preferred to provide a more homogeneous product, but occasional mixing every 3–5 minutes for approximately 1 hour will suffice. Allow the slurry to stand overnight. The next day pour off or suction filter off the excess methanol. Rinse the resin either batch-wise or by a flow-through column method with 5–10 bed volumes of water.

The following are some examples of synergistically stabilized, mixed form complexes of the present invention. These examples serve to illustrate various methods of practicing the invention and are not intended as limitations to the scope of the invention. The specific amounts described in these examples can be scaled up to provide larger quantities as desired or changed to provide any degree of or combination of loading on the resin.

EXAMPLE I

For 18.74 grams of dry virgin resin material (poly-4-vinylpyridine, crosslinked or P4VP) (8.8 meq/gram), add 12.56 grams of $I_2$ and 8.03 grams of iodine monochloride (ICl) to approximately 100 mL of methyl alcohol. After the $I_2$ and ICl are dissolved, add the resin and mix, let stand overnight, and rinse as described in the general procedure above. For this resin 30% of the available pyridyl sites are complexed with $I_2$ and 30% with ICl.

EXAMPLE II

For 17.31 grams of virgin P4VP, add 19.33 grams of $I_2$ and 2.43 grams of bromine ($Br_2$) to approximately 100 mL of methyl alcohol. After the $I_2$ and $Br_2$ are dissolved, add the dry resin material, mix, let stand, and rinse as above. For this resin 50% of the pyridyl sites are complexed with $I_2$ and 10% with $Br_2$.

EXAMPLE III

Follow the same procedure for EXAMPLE II except substitute 2.47 grams of ICl for the $Br_2$. This resin is comprised of 50% $I_2$ and 10% ICl (as percent available pyridyl functional sites).

EXAMPLE IV

For 17.31 grams of virgin P4VP, add 12.17 grams of $Br_2$ and 1.76 grams of bromine chloride (BrCl) in approximately 100 mL of chloroform ($CHCl_3$). After the $Br_2$ and BrCl are dissolved in the $CHCl_3$, add the dry resin material, mix, let stand, and rinse as above. This resin is comprised of 50% $Br_2$ and 10% BrCl (as percent available pyridyl functional sites).

EXAMPLE V

Follow the same procedure for EXAMPLE IV except substitute 15.75 grams of iodine monobromide (IBr) for the $Br_2$. This resin is comprised of 50% IBr and 10% BrCl (as percent available pyridyl functional sites).

EXAMPLE VI

For 6.68 g of the dry virgin poly-2-vinylpyridine (crosslinked) resin (8.5 meq/gram), add 7.21 grams of $I_2$ and 0.92 grams of ICl to approximately 100 mL of methyl alcohol. After the $I_2$ and ICl are dissolved, add the resin, mix, let stand, and rinse as above. This resin is comprised of 50% of $I_2$ and 10% ICl (as percent available pyridyl sites).

EXAMPLE VII

Follow the same procedure for EXAMPLE VI except substituted 0.91 grams of $Br_2$ for the ICl. This resin is comprised of 50% $I_2$ and 10% $Br_2$ (as percent available pyridyl sites).

EXAMPLE VIII

For 34.62 g of dry virgin P4VP, add 15.46 g of $I_2$ and 4.87 g of $Br_2$ to approximately 100 mL of methyl alcohol. After the $I_2$ and $Br_2$ are dissolved, add the dry resin material, mix, let stand, and rinse as above. This resin is comprised of 20% $I_2$ and 10% $Br_2$ (as percent available pyridyl sites).

EXAMPLE IV

Follow the same procedure for EXAMPLE VIII, except use 11.6 g of $I_2$ and 7.3 g of $Br_2$. This resin is comprised of 15% $I_2$ and 15% $Br_2$ (as percent available pyridyl sites).

Table I shows the effluent composition of some of the previous state-of-the-art iodinated resins compared to the present invention's mixed form halogenated and/or interhalogenated resins upon treatment with three different feed waters. All of the mixed form resins of the present invention shown in Table I were prepared in accordance with the methods described above.

The following results disclose problems apparently not recognized in the prior art. Table I shows that for the three different feed waters illustrated therein each of the last three resins (X, Y, and Z) release halide ion ($I^-$) and polyhalide ion ($I_3^-$,) with at least one of the waters. In contrast, none of the mixed form halogenated and/or interhalogenated resins release $I^-$. Each of the mixed form halogenated and/or interhalogenated resins release both iodine ($I_2$) and hypoiodous acid (HOI) or bromine, hyopbromous acid (HOBr) and/or hypoiodous acid in near equal or significant levels.

TABLE I

| | | Iodine composition determination for effluents from Iodinated and(or) Interhalogenated resins | | | | | | | |
|---|---|---|---|---|---|---|---|---|---|
| | | Iodine composition in effluents (mg/L)[b] | | | | | | | |
| | | For distilled water feed[c] | | | For $Cl_2$—free tap water feed[d] | | | For 250 mg $Cl^-$/L feed[e] (as NaCl) | | |
| RESIN | FORM | $I_2(I°)$ | $I^-$ | $HOI(I^+)$ | $I_2(I°)$ | $I^-$ | $HOI(I^+)$ | $I_2(I°)$ | $I^-$ | $HOI(I^+)$ |
| EXAMPLE I[a] | 30% $I_2$/30% ICl | 3.1 | 0 | 4.75 | 3.2 | 0 | 17.1 | 3.3 | 0 | 2.5 |
| EXAMPLE II[a] | 50% $I_2$/10% $Br_2$ | 2.1 | 0 | 3.05 | 2.8 | 0 | 7.5 | 2.0 | 0 | 5.55 |
| EXAMPLE III[a] | 50% $I_2$/10% ICl | 3.5 | 0 | 5.05 | 3.2 | 0 | 6.5 | 3.1 | 0 | 4.2 |
| EXAMPLE V[a,i] | 50% IBr/10% BrCl | 0.08 | 0 | 0.35 | 1.4 | 0 | 3.05 | 0.5 | 0 | 2.45 |
| EXAMPLE VI[j] | 50% $I_2$/10% ICl | 15.0 | 0 | 5.3 | 7.1 | 0 | 8.05 | 10.6 | 0 | 5.1 |
| EXAMPLE VII[j] | 50% $I_2$/10% $Br_2$ | 11.9 | 0 | 10.9 | 13.2 | 0 | 12.2 | 9.8 | 0 | 11.9 |
| EXAMPLE VIII[k] | 20% $I_2$/10% $Br_2$ | 0.52 | 0 | 0.05 | 0.7 | 0 | 3.7 | 0.68 | 0 | 0.03 |
| EXAMPLE IX[k] | 15% $I_2$/15% $Br_2$ | 0.28 | 0 | 0.12 | 1.8 | 0 | 4.6 | 0.2 | 0 | 1.4 |
| X[a,f] | 66% $I_2$ | 3.0 | 0.13 | 0 | 7.8 | 0 | 0 | 2.7 | 0.43 | 0 |
| Y[g] | 100% $I_3^-$ | 0.42 | 0.88 | 0 | 0.74 | 8.5 | 0 | 0.23 | 18.1 | 0 |
| Z[h] | 60% $I_3^-$/20% $I_5^-$ | 1.7 | 0 | 2.3 | 2.9 | 0 | 3.4 | 1.9 | 0.65 | 0 |

[a]Base resin is poly-4-vinylpyridine, crosslinked with 2% divinylbenzene (10 × 35 mesh). This material was treated with the appropriate amount of halogen and(or) interhalogen to give the specified formulation. Each resin (6.0 mL) was placed in a 1-cm i.d. glass column and operated at 24 mL/min. (gravity flow). The %-form represents the percent of available complexing sites converted to that form.
[b]Analyzed by modified standard leuco crystal violet method.
[c]Buffered to pH 7 by dropwise addition of dilute sodium carbonate.
[d]Tap water was dechlorinated by passing through a fresh bed of granular activated carbon.
[e]Added 412 mg NaCl/L of distilled water and buffered to pH 7 as in [c] above.
[f]Resin X is single-form, free base resin according to U.S. Pat. No. 3,565,872.
[g]Resin Y is triiodide ($I_3^-$)-form, anion exchange resin (20 × 40 mesh) according to U.S. Pat. No. 3,187,860.
[h]Resin Z is mixed form polyhalide resin (60% $I_3^-$/20% $I_5^-$-form) (20 × 40 mesh) according to U.S. Pat. No. 4,187,183.
[i]Effluents from Resin EXAMPLES II, V, and VII may contain mixtures of HOI, $Br_2$, and(or) HOBr. Residuals are expressed as HOI and $I_2$.
[j]Base resin is poly-2-vinylpyridine crosslinked with 2% divinylbenzene.
[k]Same as in footnote [a], except 100-mL bed and ~380 mL/min. flow rate.

Also, samples of single-form resins according to U.S. Pat. No. 3,565,872 ($Cl_2$—, $Br_2$—, and BrCl—forms) were prepared and were found to undergo severe resin decomposition within hours or weeks after preparation. After one year of standing in aqueous medium, these resins were incapable of releasing detectable levels (<0.01 mg/L) of halogen residual. In contrast, the mixed form resins prepared according to the present invention which contained $Br_2$ or BrCl (EXAMPLES II, V, and VII) exhibited no detectable resin decomposition and EXAMPLE IV ($Br_2$/BrCl—mixed form) exhibited only moderate degradation after one year in aqueous medium. These mixed form resins (EXAMPLES II, IV, V, and VII), after one year in aqueous medium still released disinfecting levels (≦0.50 mg/L) of halogen and/or hypohalous acid. This heretofore unknown synergistic stability demonstrated by EXAMPLES II, IV, V, and VII is but one of the unique advantages of the present invention over the prior art and is believed to occur to some degree in all of the mixed form resins.

To further demonstrate the unobvious advantages of the present invention, the degree of resin degradation (swelling) and effluent composition of several resins are compared in Table II. Resins A and B were prepared according to U.S. Pat. No. 3,565,872. Although resin A (15% $I_2$) does not exhibit degradation (no swelling), it has the disadvantage of releasing iodide ($I^-$). Resin B (15% $Br_2$) exhibits significant swelling indicating resin degradation. However, EXAMPLES VIII and IX which are the mixed-form resins do not exhibit resin degradation and both release a mixture of iodine and hypoiodous acid (HOI)(also see Table I).

Table III shows the on-contact, instantaneous disinfection efficiency of the various halogenated and/or interhalogenated vinylpyridine resins prepared in accordance with the present invention. Note particularly the poor disinfection efficiency of the untreated resin, i.e., the virgin granular crosslinked poly-4-vinylpyridine, as compared to the other resins in Table III.

As illustrated in Tables I and III, EXAMPLES I and II are the preferred embodiments since both iodine ($I_2$) and hypoiodous acid (HOI) or iodine and bromine ($Br_2$) are produced in the effluent

TABLE II

Comparison of resin stability and effluent composition of various resins

| RESIN[a] | % Sites Converted | | Observed Swelling[b] Due to Resin Degradation | % Swelling[b] | Effluent Composition[c] (mg/L) | | | |
|---|---|---|---|---|---|---|---|---|
| | % $I_2$ | % $Br_2$ | | | $I_2(I°)$ | $I^-$ | HOI($I^+$) | $Br_2$ |
| EXAMPLE VIII | 20 | 10 | no | 0 | 0.52 | 0 | 0.05 | ~0 |
| EXAMPLE IX | 15 | 15 | no | 0 | 0.28 | 0 | 0.12 | ~0 |
| A[d] | 15 | 0 | no | 0 | 0.84 | 1.22 | 0 | — |
| B[d] | 0 | 15 | yes | 15% | — | — | — | 0.2 |

[a]100-mL bed volume; flow rate = ~380 mL/min.
[b]at ~1 month after preparation and standing in aqueous solution (deionized water).
[c]feed water is pH 7-buffered deionized water (see footnote [c] in Table I).
[d]prepared according to U.S. Pat. No. 3,565,872.

TABLE III

On-contact, instantaneous disinfection efficiency of mixed form halogenated and(or) interhalogenated free base vinylpyridine resins

| RESIN | FORM[b] | Bacteria Level Influent | E. coli[c]/mL in Effluent | Total Halogen Concentration in Effluent[d] |
|---|---|---|---|---|
| EXAMPLE I[a] | 30% $I_2$/30% ICl | 700,000 | <1 | 8.2 mg/L as $I_2$ |
| EXAMPLE II[a] | 50% $I_2$/10% $Br_2$ | 950,000 | <1 | 10.5 mg/L as $I_2$ |
| EXAMPLE III[a] | 50% $I_2$/10% ICl | 950,000 | <1 | 8.5 mg/L as $I_2$ |
| EXAMPLE IV[a] | 50% $Br_2$/10% BrCl | 700,000 | <1 | 12.5 mg/L as $Br_2$ |
| EXAMPLE V[a] | 50% IBr/10% BrCl | 700,000 | <1 | 8.5 mg/L as $I_2$ |
| EXAMPLE VI[e] | 50% $I_2$/10% ICl | 700,000 | <1 | 36.0 mg/L as $I_2$ |
| EXAMPLE VII[e] | 50% $I_2$/10% $Br_2$ | 700,000 | <1 | 26.0 mg/L as $I_2$ |
| (virgin resin)[f] | — | 700,000 | 350,000 | — |

[a]Base resin is granular poly-4-vinylpyridine, crosslinked with 2% divinylbenzene (10 × 35 mesh). This material was treated with the appropriate halogen and(or) interhalogen to give the desired formulation. Each resin (~50 mL) was placed in a glass column (¾" i.d.) and operated at 140 mL/min. (gravity flow).
[b]%-form represents percent of available pyridine sites converted to that form.
[c]Each column was flushed with 100 mL of sterile, buffered distilled water and then challenged with 100 mL of the bacterial suspension. The final 50 mL of the bacterial challenge water was collected in a sterile bottle containing 0.2 mL of 10% sodium thiosulfate. One mL of the challenge effluent was tested for E. coli, ATCC #8739.
[d]Effluents from resin EXAMPLES I, III, and VI contain mixtures of $I_2$ and HOI. Effluents from resin EXAMPLES II, IV, and VII contain mixtures of $I_2$ and $Br_2$ or HOI, $Br_2$, and(or) HOBr. Analyzed by standard DPD method.

at a total active halogen level of aproximately 8–10 ppm. This level of iodine and/or bromine is adequate for essentially complete disinfection of moderately and heavily contaminated water. The molecular iodine ($I_2$) and bromine ($Br_2$) are most effective against amoebic cysts and the hypoiodous acid is desirable since it is more bactericidal and at least 40 times more virucidal than iodine.

Not only is instantaneous, on-contact disinfection achieved with the mixed form resins, but halogen residuals are also produced to provide for protection against post-disinfection recontamination. If the final use of the treated water requires that the halogen and the hypohalous acid be removed, both may be effectively removed by employing an activated charcoal follow-up scavenger column or bed in the water treatment system. If a lower level of halogen and hypohalous acid are desired in the effluent, the resin can be prepared initially with a lower weight percent of halogens and/or interhalogens.

Various modes of carrying out the invention are contemplated as being within the scope of the following claims particularly pointing out and distinctly claiming the subject matter which is regarded as the invention.

I claim:

1. A stable, mixed form halogenated and/or interhalogenated molecular addition reaction product comprising a copolymer in the form A/B-X, wherein X includes polyvinylpyridine having the cyclic pyridyl functional ring group $C_5H_5N$ crosslinked with about 2-25% divinylbenzene, and A/B is a combination of halogens and/or interhalogens bonded to the nitrogen atom of the pyridyl functional group of X and selected from the group consisting of $I_2/ICl$, $I_2/IBr$, $I_2/Br_2$, $I_2/BrCl$, $Br_2/BrCl$, $Br_2/ICl$, $Br_2/IBr$, $BrCl/ICl$, $BrCl/IBr$, $ICl/IBr$, and mixtures thereof, such that at least about 10% of the pyridyl functional groups are complexed by the combination A/B in proportions such that A to B is present in the molar ratio of from about 0.08 to about 0.92.

2. The product of claim 1 wherein X is poly-4-vinylpyridine crosslinked with divinylbenzene.

3. The product of claim 1 wherein X is poly-2-vinylpyridine crosslinked with divinylbenzene.

4. The product of claim 1 wherein said mixtures of A/B include a combination of three halogens and/or interhalogens.

5. The product of claim 1 wherein said mixtures of A/B include a combination of four halogens and/or interhalogens.

6. The product of claim 1 wherein said mixtures of A/B include a combination of five halogens and/or interhalogens.

* * * * *